US009480270B2

(12) United States Patent
Jensen et al.

(10) Patent No.: US 9,480,270 B2
(45) Date of Patent: Nov. 1, 2016

(54) LOW POST-ACIDIFYING LACTIC ACID BACTERIA

(75) Inventors: Niels Bang Siemsen Jensen, Frederiksberg (DK); Annette Helle Johansen, Copenhagen (DK)

(73) Assignee: Chr. Hansen A/S, Hoersholm (DK)

(*) Notice: Subject to any disclaimer, the term of this patent is extended or adjusted under 35 U.S.C. 154(b) by 1371 days.

(21) Appl. No.: 12/304,868

(22) PCT Filed: Jun. 22, 2007

(86) PCT No.: PCT/EP2007/056252
§ 371 (c)(1),
(2), (4) Date: Sep. 18, 2009

(87) PCT Pub. No.: WO2007/147890
PCT Pub. Date: Dec. 27, 2007

(65) Prior Publication Data
US 2010/0021586 A1    Jan. 28, 2010

(30) Foreign Application Priority Data

Jun. 23, 2006 (EP) .................................. 06115993

(51) Int. Cl.
*A23C 9/123* (2006.01)
*A23C 11/10* (2006.01)
*C12N 15/01* (2006.01)
*C12R 1/225* (2006.01)

(52) U.S. Cl.
CPC ........... *A23C 9/1238* (2013.01); *A23C 11/106* (2013.01); *C12N 15/01* (2013.01); *C12R 1/225* (2013.01); *A23Y 2220/15* (2013.01)

(58) Field of Classification Search
USPC ........................................................ 426/34
See application file for complete search history.

(56) References Cited

U.S. PATENT DOCUMENTS

| 5,545,554 | A   |   | 8/1996  | Germond et al. |
|-----------|-----|---|---------|----------------|
| 5,866,385 | A   | * | 2/1999  | Dickely et al. ................ 435/6.1 |
| 7,037,538 | B2  | * | 5/2006  | O'Sullivan et al. ............ 426/34 |
| 2006/0240539 | A1 | * | 10/2006 | Horvath et al. ........... 435/252.5 |

FOREIGN PATENT DOCUMENTS

| EP | 0 518 096     | 12/1992 |
|----|---------------|---------|
| EP | 0 638 642 A1  | 2/1995  |
| WO | WO 2006/063142 A3 | 6/2006 |

OTHER PUBLICATIONS

Hess et al, Rheological Properties of Nonfat Yogurt Stabilized Using *Lactobacillus delbruckuu* ssp. *bulgaricus* Producing Exopolysaccharide or Using Commerical Stabilizer Systems, Journal of Dairy Science, vol. 80, No. 2, 1997.*
Krasaekoopt et al, Comparison of Texture of Yogurt Made from Conventionally Treated Milk and UHT Milk Fortified with Low-heat Skim Milk Powder, Food Engineering & Physycal Properites, Jounral of Food Science, vol. 69, Issue 6, May 2006.*

(Continued)

*Primary Examiner* — D Lawrence Tarazano
*Assistant Examiner* — Philip Dubois
(74) *Attorney, Agent, or Firm* — Foley & Lardner LLP

(57) ABSTRACT

The present invention relates to lactic acid bacteria that have low or reduced post-acidification properties, and to a method for providing such bacteria. Also, the invention relates to the use of such bacteria for manufacturing of fermented dairy products, and to dairy products containing the bacteria.

6 Claims, 3 Drawing Sheets

(56) References Cited

OTHER PUBLICATIONS

Figure 1:
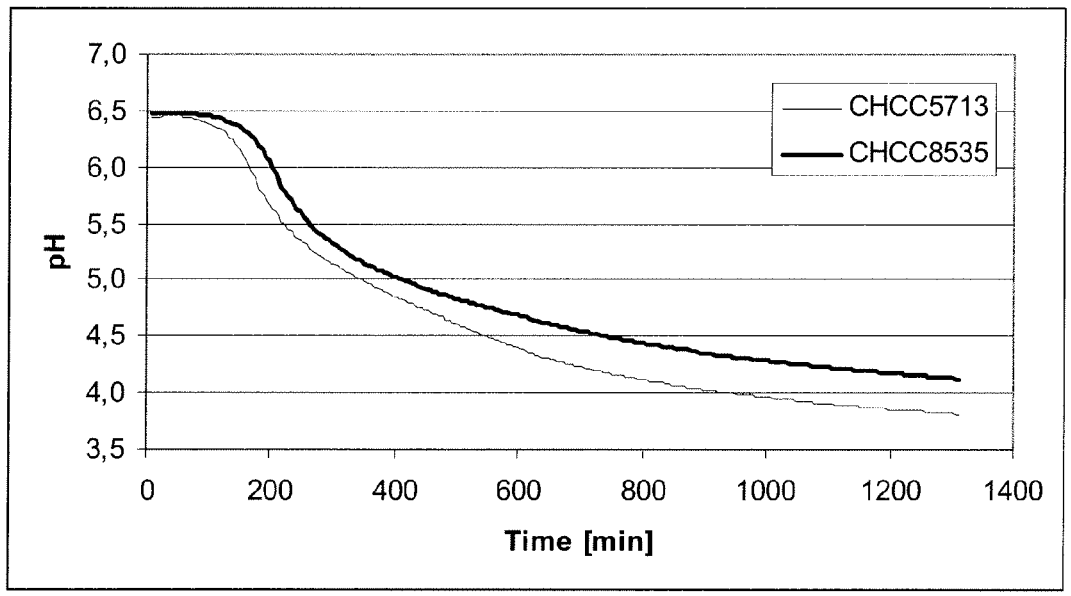

Frances Arnold, Design by Direted Evolution, A. Che. Res. 1998, 31, 125-131 (1997).*

C. Moller et al., "Isolierung von *Lactobacillus delbrueckii* subsp. *bulgaricus* Mutanten zur Herstellung eines Joghurts mit milder Geschmackscharakteristik", Kiel. Milchwirtsch. Forschungsber. ISSN 0023-1347, vol. 53, 2001, pp. 167-185 XP009073581.

* cited by examiner

LOW POST-ACIDIFYING LACTIC ACID BACTERIA

FIELD OF INVENTION

The present invention relates to lactic acid bacteria that have low or reduced post-acidification properties, and to a method for providing such bacteria. Also, the invention relates to the use of such bacteria for manufacturing of fermented dairy products, and to dairy products containing the bacteria.

BACKGROUND OF INVENTION

Strains of the species *Lactobacillus delbrueckii* subsp. *bulgaricus* are essential components of bacterial cultures used for the production of fermented milks and yoghurts in particular. Such strains usually produce lactic acid during the shelf life of the dairy products fermented with the bacterial cultures of which the strains are a component. This phenomenon is often referred to as "post—acidification". Such strains do not usually contribute to the increased texture of the dairy products obtained by fermentation with the bacterial cultures of which the strains are a component.

According to the legislation in most EU countries, starter cultures to be used for the production of yoghurt must be composed of strains of the type *Lactobacillus bulgaricus* and strains of the type *Streptococcus thermophilus*. Furthermore, the acidification of milk takes place faster when starter cultures are composed of both types of strains, rather than one single type of strain alone.

A trend in the market for fermented milks is products with a moderate to a non-existent development of acidity during shelf life (low post-acidification) and a high texture (or viscosity). When selecting strains of the type *Lactobacillus delbrueckii* subsp. *bulgaricus* to be used either alone or as component of a culture for production of fermented milk and yoghurt, the product developer has to choose between the known strains that have the following combination of properties:

low post-acidification and low texturing power; or
high post-acidification and low texturing power; or
high post-acidification and high texturing power, as no *Lactobacillus delbrueckii* subsp. *bulgaricus* strains that in a satisfactory way combine a low post-acidification profile and a high texturing profile are available.

Using any of the above known strains, the fermented milk product will either result in a high degree of post-acidification or a low texture, resulting from the use of the bacterial culture. The dairies often choose to work with cultures where the *Lactobacillus delbrueckii* subsp. *bulgaricus* strains combine low post-acidification and low texture. To increase texture in the fermented milk product, they add thickening agent(s) to the milk base before the fermentation takes place.

SUMMARY OF INVENTION

The problem faced by the skilled person is to provide alternative *Lactobacillus delbrueckii* subsp. *bulgaricus* strains that combine a low post-acidification profile and a high texturing profile, thereby making the addition of thickening agents superfluous. Several scientists have tried to obtain such strains, but without any success. In Möller et al. (2001) chemical mutagenesis (with the mutagen MNNG (N-methyl-N-nitroso-N-nitroguanidin)) of a strain of *Lactobacillus delbrueckii* subsp. *bulgaricus* (Visby strain 231) is carried out in order to obtain mutants with less post-acidification. The mutagenised strain was plated manually and colonies transferred manually to microtiter plates containing milk. After incubation the pH was measured well by well by for approximately 2000 isolates by use of a microelectrode. Four mutants with higher end-pH than the mother strain were isolated. The described mutagenesis and screening did not result in any mutants with high texture and low post-acidification.

The present inventors have surprisingly shown that it indeed is possible to provide such strains, and they have developed a method for providing such strains, said method differs from the method of Möller et al (2001) in that the present inventors use high texturing strains as mother strains and that a weak mutagen is used. Performing the method of the invention, the present inventors have surprisingly identified stains having improved texturing properties relative to their mother strains. Thus, the present inventors have devised a method to develop *Lactobacillus delbrueckii* subsp. *bulgaricus* strains, which substantially contribute to an increased texture of the dairy products obtained by fermentation by a strain of the invention, or by bacterial cultures of which a strain of the invention is a component, without significantly post-acidifying the dairy products.

The resulting dairy products are characterized by a pleasant mild, less sour taste than previously known products.

DETAILED DISCLOSURE

In a first aspect, the present invention relates to a *Lactobacillus delbrueckii* subsp. *bulgaricus* strain that:
a) produces less acid when present in a fermented dairy product (e.g. during storage) than other highly texturing strains of the same species; and/or
b) increase the texture of the dairy product fermented with the strain to a higher level than low post-acidifying strains of the same species.

Interesting embodiments of such a strain are a strain that
a) has a pH, measured in a standard assay (assay for determination of post-acidifying properties) in the range of 4.25-4.55 (such as in the ranges of 4.30-4.55; or in the range of 4.35-4.55) after 14 days and/or after 21 days and/or after 28 days of storage; and
b) has a texturing property, measured in Pa using the assay for determination of viscosity, of not less than 25 (such as not less than 30; not less than 35; not less than 39; not less than 42; not less than 44; not less than 45; not less than 46; not less than 47; not less than 48; or not less than 50);
or a strain that
a) decreases the pH, measured in a standard assay (assay for determination of post-acidifying properties) less than 0.30 pH units (such as less than 0.20 pH units) after 14 days of storage; and
b) has a texturing property, measured in Pa using the assay for determination of viscosity, of not less than 25 (such as not less than 30; not less than 35; not less than 39; not less than 42; not less than 44; not less than 45; not less than 46; not less than 47; not less than 48; or not less than 50);
or a strain that
a) decreases the pH, measured in a standard assay (assay for determination of post-acidifying properties) less than 0.20 pH units (such as less than 0.15; less than 0.11; less than 0.08; less than 0.07; less than 0.06; less than 0.05; less than 0.04; less than 0.03; or even less than 0.02 pH units) at 8 degrees C. after 7 days of storage; and
b) has a texturing property, measured in Pa using the assay for determination of viscosity, of not less than 25 (such as not less than 30; not less than 35; not less than 39; not less than 42; not less than 44; not less than 45; not less than 46; not less than 47; not less than 48; or not less than 50).

By the term "decreases the pH" should be understood the decrease of the pH relative to the starting point, i.e. a pH of 4.55. A decrease of e.g. 0.30 pH units means that the resulting pH is 4.25.

In two interesting embodiments, the decreased acid production is not due to a significant or complete inactivation of the beta galactosidase activity; and/or not due to a significant or complete inactivation of the lactate dehydrogenase activity. By the term "not due to a significant inactivation" is understood a reduction of activity of less than 30% (such as less than 20% or even less than 10%).

Presently preferred is a *Lactobacillus delbrueckii* subsp. *bulgaricus* strain which is selected from the group consisting of: CHCC10019; CHCC8535; and CHCC7159; and mutants of any of these (such as functional equivalent mutants, e.g. mutants which have substantially the same post-acidifying and texturing properties, and most preferred is the strain CHCC7159 or a mutant thereof, such as a functionally equivalent mutant, e.g. a mutant that has substantially the same post-acidifying and texturing properties.

In the present context, the term "mutant thereof" should be understood as a strain derived from a strain of the invention by means of e.g. genetic engineering, radiation and/or chemical treatment. It is preferred that the mutant is a functionally equivalent mutant, e.g. a mutant that has substantially the same post-acidifying and texturing properties as the mother strain. Such a mutant is a part of the present invention. Especially, the term "mutant thereof" refers to a strain obtained by subjecting a *Lactobacillus delbrueckii* subsp. *bulgaricus* strain of the invention (such as CHCC10019; CHCC8535; CHCC7159; CHCC3984; CHCC3606 or CHCC5713) to any conventionally used mutagenization treatment including treatment with a chemical mutagen such as ethane methane sulphonate (EMS) or N-methyl-N'-nitro-N-nitroguanidine (NTG), UV light or to a spontaneously occurring mutant. The mutant strain should preferably fulfil at least one of the a) and b) combinations above. Although it is presently preferred to provide the strain by random mutagenesis or by selection of spontaneously occurring mutants, i.e. without the use of recombinant DNA-technology, it is envisaged that mutants of *Lactobacillus delbrueckii* subsp. *bulgaricus* can be provided by such technology including site-directed mutagenesis and PCR techniques and other in vitro or in vivo modifications of DNA sequences. The term "substantially the same post-acidifying property" should preferably be understood as the pH value may vary up to ±0.1 pH units (such as 0.05, 0.01, or 0.00 units) relative to the mother strain, and the term "substantially the same texturing property" should preferably be understood as the Pa value may vary up to 20% (e.g. up to 10% or up to 5%) and/or +10/−2 units (such as +5, +3, +/−2, +/−1.0, +/−0.5 or 0.0 units) relative to the mother strain.

In a second aspect, the present invention relates to a method for providing a *Lactobacillus delbrueckii* subsp. *bulgaricus* strain that produces less acid when present in a fermented dairy product (e.g. during storage of the finished product) compared to a mother strain, the method comprises treating a strain of *Lactobacillus delbrueckii* subsp. *bulgaricus* (the mother strain) with a mutagen (preferably a mild or weak mutagen), such as a mutagen selected from the group consisting of: Ethyl methane sulfonate (e.g. 1%); Nitrous acid (e.g. 0.05 M); Methyl methane sulfonate (e.g. 20 mM); Nitrosoguanidine (e.g. 25 µM); and ICR-170 acridine mustard (e.g. 5 µg/ml), or with radiation, such as with X rays (e.g. 2000 r/min); or UV rays (e.g. 600 erg/mm2 per min). Presently preferred is the mutagen EMS (Ethyl methane sulphonate).

It is presently preferred that the mother strain is a strain of *Lactobacillus delbrueckii* subsp. *bulgaricus* which is highly texturing upon growth in milk, but also is highly post-acidifying, such a strain is selected among the stains that have the following properties:
a) high texturing property, such as a strain that measured using the assay for determination of viscosity, has a Pa of not less than 25 (such as not less than 30; not less than 35; not less than 39; not less than 42; not less than 44; not less than 45; not less than 46; not less than 47; not less than 48; or not less than 50); and
b) high post-acidification property, such as a strain that decreases the pH, measured in a standard assay (assay for determination of post-acidifying properties) more than 0.20 (such as more than 0.30 or 0.40, or even more than 0.50) pH units after 7 days of storage.

Examples of such a strain are CHCC3984, CHCC3606 and CHCC5713, and mutants of any of these (such as functional equivalent mutants, e.g. mutants which have substantially the same post-acidifying and texturing properties). These strains, as well as the strains of *Lactobacillus delbrueckii* subsp. *bulgaricus* which are obtainable by the method of the invention, are all a part of the present invention.

In an interesting embodiment, the method of the invention further comprises:
incubating individual mutants in a medium (such as on pH indicator plates; in microtiter plates containing medium e.g. supplemented with a pH indicator; or in test tubes containing medium e.g. supplemented with a pH indicator); and
selecting a mutant with significant higher end-pH of the medium after incubation than the mother strain.

Conveniently, the pH in measured by a pH electrode, or by using a pH indicator such as bromophenol purple/bromophenol green, and the medium is milk, e.g. standard medium.

In a further aspect, the present invention relates to the use of a strain of *Lactobacillus delbrueckii* subsp. *bulgaricus* according to the invention for manufacturing a fermented dairy product, such as a yoghurt.

The invention also relates to a method for manufacturing a dairy product, comprising mixing a strain according to the invention with milk, as well as a dairy product obtainable by the method. The resulting dairy products are characterized by a pleasant mild and less sour taste than previously known products.

In a still further aspect, the invention relates to a method for propagation of a *Lactobacillus delbrueckii* subsp. *bulgaricus* bacterium, comprising mixing a strain of the invention, or a composition comprising said strain, with a growth medium, such as milk (e.g. standard medium).

In a last aspect, the invention relates to a composition usable for fermenting milk, comprising a strain of *Lactobacillus delbrueckii* subsp. *bulgaricus* according to the invention. An example of such a composition is a starter culture, which besides the strain of the invention contains further strains or additives for preservation. The composition may be in dried, freeze-dried, frozen or liquid form.

DEFINITIONS

In the present context, the term "milk" includes fat-free milk, low fat milk, full fat milk, lactose-free milk (produced by hydrolyzing the lactose by lactase enzyme to glucose and galactose, or other method), concentrated milk or dry milk. Fat-free milk is non-fat or skim milk product. Low-fat milk is typically defined as milk that contains from about 1% to about 2% fat. Full fat milk often contains 2% fat or more. As used herein, the term "milk" is also intended to encompass milks from animal and plant sources. Animal sources of milk include, but are not limited to, human, cow, sheep, goat, buffalo, camel, llama, mare and deer. Plant sources of milk include, but are not limited to, milk extracted from soybean or oat. In addition, the term "milk" refers to not only whole milk, but also skim milk or any liquid component derived therefrom.

By the term "high texturing strain" should be understood a strain that when used to inoculate a standard medium at a ratio of $1\times10^5$-$1\times10^6$ cfu/g, at a temperature of incubation of 43° C., until a pH of 4.55, brings about a shear stress of the fermented milk superior to 25 Pa, when assessed instrumentally 20 hours after the end of fermentation/coagulation as described in "Assay for determination of viscosity". Conversely, by the term "low texturing strain" should be understood a strain that when used to inoculate a standard medium at a ratio of $1\times10^5$-$1\times10^6$ cfu/g, at a temperature of incubation of 43° C., until a pH of 4.55, brings about a shear stress of the fermented milk inferior to 25 Pa, when assessed instrumentally 20 hours after the end of fermentation/coagulation as described in the assay for determination of viscosity.

By the term "high post-acidifying strain" should be understood a strain that when grown in accordance with "Assay for determination of post-acidifying properties" decreases the pH more than 0.20 pH units after 7 days of storage (the pH is lowered from 4.55 to 4.35 or lower). Conversely, by the term "low post-acidifying strain" should be understood a strain that when grown in accordance with "Assay for determination of post-acidifying properties" decreases the pH no more than 0.20 pH units after 7 days of storage (the pH is lowered from 4.55 to 4.35 or to a pH value in the range 4.55 to 4.35, both end points included).

By the term "standard medium" should be understood milk reconstituted from skimmed milk powder, having a dry matter content of 9.5%, and has been heat treated to 99 degrees C. for 15 minutes in a batch process.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising", "having", "including" and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

LEGENDS TO THE FIGURES

FIG. 1 depicts a pH vs. time plot at 43° C. of the mutant strain CHCC8535 and the mother strain CHCC5713. Cf. Example 1.

Figure 2:
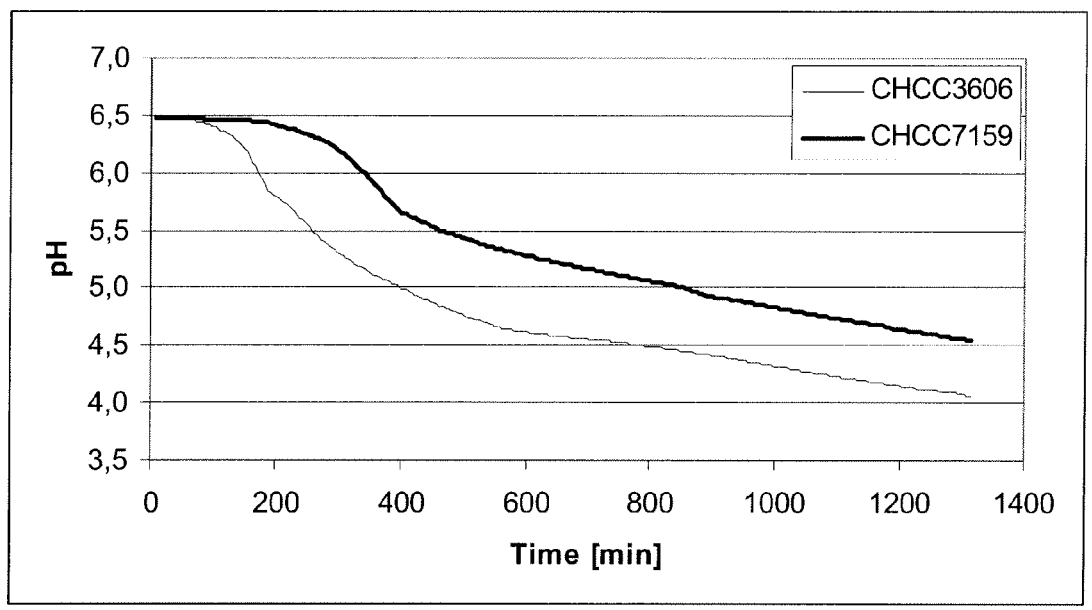

FIG. 2 depicts a pH vs. time plot at 43° C. of the mutant strain CHCC7159 and the mother strain CHCC3606. Cf. Example 1.

Figure 3:
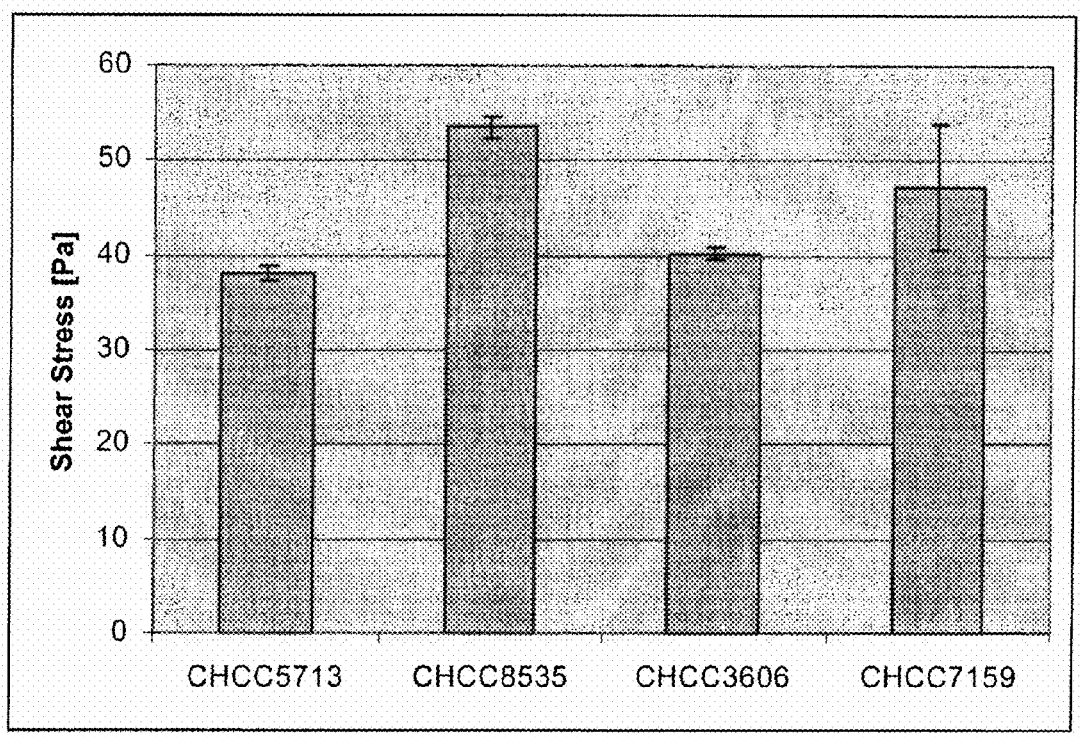

FIG. 3 depicts the average of shear stress measured on three independent samples produced with different strains of the type *Lactobacillus delbrueckii* subsp. *bulgaricus*. Error bars span 2 standard deviations around averages. Cf. Example 1.

Figure 4:
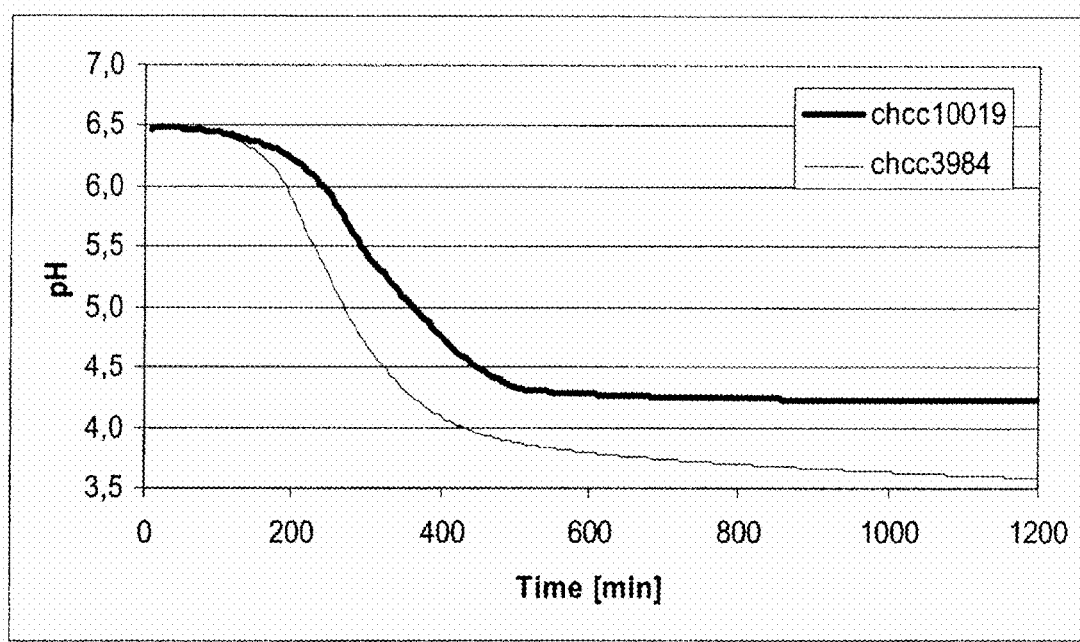

FIG. 4 depicts a pH vs. time plot at 43° C. of the mutant strain CHCC10019 and the mother strain CHCC3984. Cf. Example 2.

Figure 5:
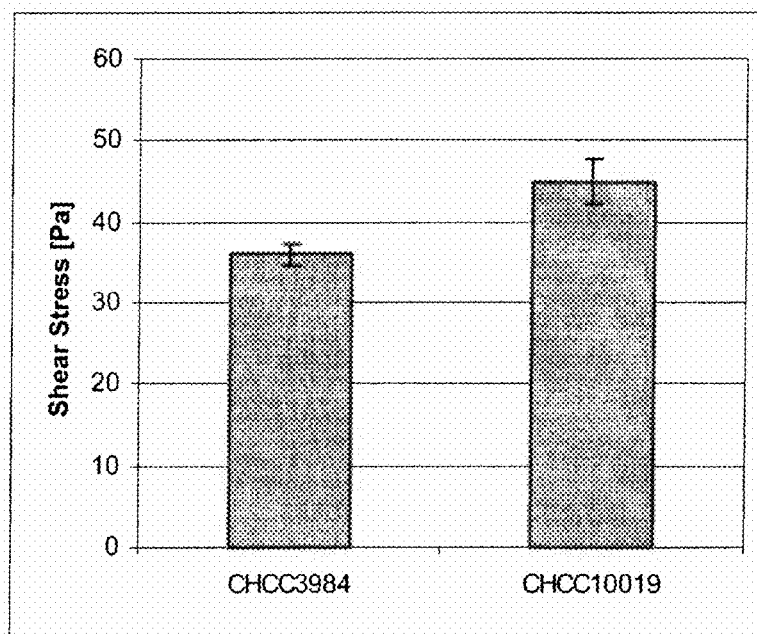

FIG. 5 depicts the average of shear stress measured on three independent samples produced with mutant strain CHCC10019 and the mother strain CHCC3984. Error bars span 2 standard deviations around averages. Cf. Example 2.

EXAMPLES

General Methods

According to a method of the invention, a mother strain of *Lactobacillus delbrueckii* subsp. *bulgaricus* that has high texturing properties and high post-acidifying properties is treated with a chemical mutagen. The resulting strains are screened for mutants having low post-acidifying properties, and the desired mutants are thereafter screened for high texturing properties. The method is described in more details below:

Assay for Determination of Viscosity (Texturing Properties)

Frozen concentrates of the strain are used to inoculate 200 mL milk reconstituted from skimmed milk powder (the standard medium). The milk had a dry matter content of 9.5% and had been heat treated to 99° C. for 15 minutes in a batch process at ambient pressure. Frozen concentrates of *Lactobacillus bulgaricus* typically display a cell count between $1\cdot10^9$ and $1\cdot10^{10}$ cfu/g. The rate of inoculation was 1 g concentrate per 10 L milk, hence between $1\cdot10^5$ and $1\cdot10^6$ cfu/mL milk. The incubation took place at 43° C. until pH reached 4.55, at which time the coagulation of the milk had taken place. The fermented milk was then cooled to 5° C. under periodically stirring (by placement in an ice bath for 20 minutes, thereafter in a refrigerator).

20 hours after reaching pH 4.55, the fermented milk was brought to 13° C. and stirred gently by means of a stick fitted with a bored disc (diameter=3 cm) until homogeneity of the sample. The stirring consisted of 20 up and down movements of the stick in the sample. The rheological properties of the sample were assessed at 13° C. on a rheometer (StressTech, Reologica Instruments, Sweden) equipped with a bob/cup (CC25) coaxial measuring system.

The viscometry test was made with shear rates varying from 0.27 to 300 1/s in 21 steps. Shear rates were increased and then decreased and the upward and downward curves of shear stress and apparent viscosity were recorded. Delay, integration and equilibrium times were 5 s, 10 s and 5 min, respectively. For further analysis shear stress at 300 s-1 was chosen.

The shear stress is measured in Pa units. By definition, viscosity equals shear stress divided by shear rate. Viscosity and shear stress are therefore directly proportional and express the same properties given that shear stress values are determined at a fixed shear rate of 300 1/s.

Assay for Determination of Post-Acidifying Properties

Frozen concentrates of the strain are used to inoculate 200 mL milk reconstituted from skimmed milk powder (the standard medium). The milk had a dry matter content of 9.5% and had been heat treated to 99° C. for 15 minutes in a batch process.

Frozen concentrates of Lactobacillus bulgaricus typically display a cell count between $1 \cdot 10^9$ and $3 \cdot 10^{10}$ cfu/g. The rate of inoculation was 1 g concentrate per 10 L milk, hence between $1 \cdot 10^5$ and $3 \cdot 10^6$ cfu/mL milk. The incubation took place at 43° C. until pH reached 4.55, at which time the coagulation of the milk had taken place. The fermented milk was then cooled to 5° C. under periodically stirring (by placement in an ice bath for 20 minutes, thereafter in a refrigerator). The pH of the cooled fermented milk was measured using a pH electrode, appropriately after 1; 7; 14; 21 and 28 days of storage.

Method for Preparing the Standard Medium

Dissolve the skimmed milk powder (Arla Ingredients, Denmark—Milex 240 medium heat milk powder) in water for not more than 30 min. The aim for the preparation of milk is a dry matter of 9.5% (w/w).

The milk should be sterilized by the following temperature profile:

|  | Temperature (° C.) | Time (min) |
|---|---|---|
| Heating | ->99 ± 1 | <20 |
| Sterilization | 99 ± 1 | 15 ± 1 |
| Cooling | 99 ± 1->40 ± 5 | <40 |

Subsequently, the milk should be stored at <7° C. The milk should not be used before the next day.

Propaqation of the Bacteria

Strains of the species Lactobacillus delbrueckii subsp. bulgaricus that increase texture in fermented milks, and that post-acidify, are well known. Such strains are preferably used as mother strains. The lactic acid bacterial strains are usually added as a liquid solution, as a freeze-dried powder or as frozen pellets to the milk to be fermented. The bacterial count of the liquid, powder and pellets may vary from $1E^6$ to $1E^{12}$ colony forming units per gram ($1 \cdot 10^6$ to $1 \cdot 10^{12}$ cfu/g), applying standard cell count techniques. The liquid, powder or pellets are usually added at levels of around 0.0005-1% to the milk.

Mutagenesis

The bacterium, such as of a strain of Lactobacillus delbrueckii subsp. bulgaricus, which gives high texture upon growth in milk, but also has a high post-acidification, is mutagenised chemically, preferably with a mild mutagen, e.g. with EMS (Ethyl methane sulphonate). EMS gives rise to random base pair substitutions in the genetic material (the chromosome and plasmids) of the mutagenised bacterium. After the mutagenesis the mutagenised cultures is plated on media.

Preferred protocol: The mother strains were inoculated from frozen stocks in MRS broth (Difco) for 24 hours at 37° C., anaerobically. For the mutagenesis, the overnight cultures were vortexed at maximum speed for 1 minute to separate putative chains of cells and treated with EMS (10 ml/ml) for 2 hours at 37° C. The EMS treatment resulted in more than 99% of killing of the cells. The EMS treated cultures were frozen at −80° C. in $^{20}$% glycerol and this stock used for the screenings.

Screening

Several thousand colonies randomly picked by a colony picking robot into microtiter plates containing 200 microL milk e.g. supplemented with a pH indicator (such as bromophenol purple/bromophenol green). Each of the wells in the microtiter plates then corresponds to a model milk fermentation. The pH of the milk in wells containing mutants are compared to the corresponding wells containing the wild type strain (a strain of Lactobacillus delbrueckii subsp. bulgaricus, which gives high texture upon growth in milk, but also has a high post-acidification, such as Lactobacillus delbrueckii subsp. bulgaricus strains, CHCC3984, CHCC3606 and CHCC5713). Mutants with significant higher end-pH of the milk after acidifications at 43° C. than the wild type strains are identified, e.g. by colorimetric assessment (using a pH indicator) or by use of a pH electrode. Acidifications in a larger scale (200 ml) are performed by recording pH in a logger system with standard pH electrodes in order to verify that the mutants give rise to less post-acidification.

In order to control that the obtained mutants had the same texturing potential as the mother strain, samples of milk were fermented with the mutants and the mother strains to same final pH values and the rheological properties of the obtained fermented milks were assessed and compared by standard techniques.

Example 1

Preparation and Properties of LB strains CHCC7159 and CHCC8535

CHCC7159 and CHCC8535 are lactic acid bacteria of the type Lactobacillus bulgaricus. These strains are able to acidify milk under industrially relevant conditions and are characterised by a low post acidification. The strain CHCC7159 is a mutant obtained from CHCC3606, to which it was compared. CHCC8535 is a mutant of CHCC5713, to which it was compared. Mutagenesis (preferred protocol) and screening was carried out as described above.

Frozen concentrates of CHCC7159, CHCC8535, CHCC3606 and CHCC5713 were used to inoculate 200 mL milk reconstituted from skimmed milk powder. The milk had a dry matter content of 9.5% and had been heat treated to 99° C. for 15 minutes in a batch process. Frozen concentrates of Lactobacillus bulgaricus typically display a cell count between $1 \cdot 10^9$ and $3 \cdot 10^{10}$ cfu/g. The rate of inoculation was 1 g concentrate per 10 L milk, hence between $1 \cdot 10^5$ and $3 \cdot 10^6$ cfu/mL milk. The incubation took place at 43° C. until pH reached 4.55, at which time the coagulation of the milk had taken place. The fermented milk was then cooled to 5° C.

A pH vs time plot shows that CHCC8535 reached pH 4.60 in less than 20 hours, proving that the strains are able to acidify milk under conditions of inoculation and incubation that are industrially relevant (FIG. 1).

A pH vs time plot shows that CHCC7159 reached pH 4.60 in around 21 hours, proving that the strains are able to acidify milk under conditions of inoculation and incubation that are industrially relevant (FIG. 2).

CHCC7159 and CHCC8535 were throughout the fermentation less acidifying than their respective mother strains. CHCC8535 showed a pH after 20 hours of 4.17, which was 0.32 pH units higher than the mother strain. CHCC7159 showed a pH after 20 hours of 4.64, which was 0.50 pH units higher than the mother strain.

CHCC7159 and CHCC8535 are able to Generate an Elevated Texture in a Fermented Milk The day after incubation, the fermented milk was brought to 13° C. and stirred gently by means of a stick fitted with a bored disc until homogeneity of the sample. The rheological properties of the sample were assessed on a rheometer (StressTech, Reologica Instruments, Sweden) equipped with a C25 coaxial measuring system. The viscometry test was made with shear rates varying from 0.27 to 300 1/s in 21 steps. Shear rates were increased and then decreased and the upward and downward curves of shear stress and apparent viscosity were recorded. Delay and integration times were 5 s and 10 s, respectively. For further analysis shear stress at 300 s-1 was chosen. Fermented milks incubated with concentrates of CHCC7159 and CHCC8535 were more texturing than fermented milks produced with their respective mother strains (FIG. 3). Recorded shear stress values were on average 45 and 55 Pa for the two mutant strains, while they were around 40 Pa or less for the mother strains.

Conclusion

The strains CHCC7159 and CHCC8535 combine the following properties:
are able to generate a high texture in a fermented milk—superior to 40 Pa under the experimental conditions tested
are able to acidify milk to pH 4.60 in less than 24 hours
reach a pH after 20 hours, which is superior to 4.15 under the experimental conditions tested Example 2

Preparation and Properties of LB strain CHCC10019

CHCC10019 is a lactic acid bacterium of the type *Lactobacillus bulgaricus*. CHCC10019 is able to acidify milk under industrially relevant conditions and is characterised by a low post acidification. The strain CHCC10019 is a mutant obtained from CHCC3984, to which it was compared. Mutagenesis and screening was carried out as described above ("preferred pro-tocol"). The mutagen used was EMS.

Overnight cultures of CHCC10019 and CHCC3984 were prepared by inoculating 10 mL milk reconstituted from skimmed milk powder. The milk had a dry matter content of 9.5% and had been heat treated to 99° C. for 15 minutes in a batch process. Biological material was taken from frozen ampoules of the respective strains. Incubation took place at 37° C. for 24 hours.

Overnight cultures of CHCC10019 and CHCC3984 were used to inoculate of 200 mL milk reconstituted from skimmed milk powder (standard medium). The milk used was the same as described above. The rate of transfer was 1%. For each strain two bottles of milk were incubated. One bottle was used to obtain an acidification curve; the second bottle was used to obtain product for determination of Theological properties.

Overnight cultures of *Lactobacillus bulgaricus* typically display a cell count between 1.106 and $1\cdot10^8$ cfu/g. The rate of inoculation was 1 g overnight culture per 100 g milk, hence between $1\cdot10^4$ and $1\cdot10^6$ cfu/mL milk.

The incubation took place at 43° C. for 20 hours. A second bottle prepared under same conditions was incubated at 43° C. until pH reached 4.55, at which time the coagulation of the milk had taken place. This bottle was cooled to 5° C. until analysis of Theological properties the following day.

A pH vs time plot shows that CHCC10019 reached pH 4.50 in around 7 hrs 30 min, proving that the strain is able to acidify milk under conditions of inoculation and incubation, that are industrially relevant, see FIG. 4.

CHCC10019 was throughout the fermentation less acidifying than its mother strain. CHCC10019 showed a pH after 20 hours of 4.22, which was 0.64 pH units higher than the mother strain.

CHCC10019 is able to generate an elevated texture in a fermented milk The day after incubation, the fermented milk was brought to 13° C. and stirred gently by means of a stick fitted with a bored disc until homogeneity of the sample. The rheological properties of the sample were assessed as described in example 1. For results see FIG. 5.

Fermented milks incubated with CHCC10019 were more texturing than fermented milks produced with CHCC3984. Recorded shear stress values were on average 45 Pa for the mutant strain, while they were around 35 Pa for the mother strains.

CHCC7159 was deposited 8 Feb. 2006 at Deutsche Sammlung von Mikroorganismen und Zellkulturen GmbH (DSM) and given the accession number DSM 17959. CHCC3606, CHCC5713 and CHCC8535 were deposited 30 Mar. 2006 at DSM and given the accession numbers DSM 18142, DSM 18143, and DSM 18144, respectively. CHCC10019 and CHCC3984 were deposited 3 Apr. 2007 and given the accession numbers DSM 19252 and DSM 19251, respectively. All deposits were made according to the Budapest treaty on the international recognition of the deposit of microorganisms for the purposes of patent procedure.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

REFERENCES

Möller, C., Bockelmann, W., and K. J. Heller, 2001. Isolierung von *Lactobacillus delbrueckii* subsp. *bulgaricus* mutanten zur herstellung eines joghurts mit milder geschmackscharakteristik. Kieler Milchwirtchaftliche forchungsberichte 53, 167-185.

WO2006/063142

EP518096A1

EP638642A

U.S. Pat. No. 5,545,554A

Guide To Short-Term Tests For Detecting Mutagenic And Carcinogenic Chemicals. Prepared for the IPCS by the International Commission for Protection Against Environmental Mutagens and Carcinogens. WHO, 1985.

http://www.inchem.org/documents/ehc/ehc/ehc51.htm

All references cited in this patent document are hereby incorporated herein in their entirety by reference.

| | | |
|---|---|---|
| 0-1 | Form PCT/RO/134 (SAFE) Indications Relating to Deposited Microorganism(s) or Other Biological Material (PCT Rule 13bis) | |
| 0-1-1 | Prepared Using | PCT Online Filing Version 3.50 (Build 0001.164) |
| 0-2 | International Application No. | |
| 0-3 | Applicant's or agent's file reference | P2253PC00 |
| 1 | The indications made below relate to the deposited microorganism(s) or other biological material referred to in the description on: | |
| 1-1 | paragraph number | page 13, line 7 |
| 1-3 | Identification of deposit | |
| 1-3-1 | Name of depositary institution | DSMZ DSMZ-Deutsche Sammlung von Mikroorganismen und Zellkulturen GmbH |
| 1-3-2 | Address of depositary institution | Mascheroder Weg 1b, D-38124 Braunschweig, Germany |
| 1-3-3 | Date of deposit | 08 Feb. 2006 (08.02.2006) |
| 1-3-4 | Accession Number | DSMZ 17959 |
| 1-5 | Designated States for Which Indications are Made | all designations |
| 2 | The indications made below relate to the deposited microorganism(s) or other biological material referred to in the description on: | |
| 2-1 | paragraph number | page 13, line 9 |
| 2-3 | Identification of deposit | |
| 2-3-1 | Name of depositary institution | DSMZ DSMZ-Deutsche Sammlung von Mikroorganismen und Zellkulturen GmbH |
| 2-3-2 | Address of depositary institution | Mascheroder Weg 1b, D-38124 Braunschweig, Germany |
| 2-3-3 | Date of deposit | 30 Mar. 2006 (30.03.2006) |
| 2-3-4 | Accession Number | DSMZ 18142 |
| 2-5 | Designated States for Which Indications are Made | all designations |
| 3 | The indications made below relate to the deposited microorganism(s) or other biological material referred to in the description on: | |
| 3-1 | paragraph number | page 13, line 9 |
| 3-3 | Identification of deposit | |
| 3-3-1 | Name of depositary institution | DSMZ DSMZ-Deutsche Sammlung von Mikroorganismen und Zellkulturen GmbH |
| 3-3-2 | Address of depositary institution | Mascheroder Weg 1b, D-38124 Braunschweig, Germany |
| 3-3-3 | Date of deposit | 30 Mar. 2007 (30.03.2007) |
| 3-3-4 | Accession Number | DSMZ 18143 |
| 3-5 | Designated States for Which Indications are Made | all designations |
| 4 | The indications made below relate to the deposited microorganism(s) or other biological material referred to in the description on: | |
| 4-1 | paragraph number | page 13, line 9 |
| 4-3 | Identification of deposit | |
| 4-3-1 | Name of depositary institution | DSMZ DSMZ-Deutsche Sammlung von Mikroorganismen und Zellkulturen GmbH |
| 4-3-2 | Address of depositary institution | Mascheroder Weg 1b, D-38124 Braunschweig, Germany |
| 4-3-3 | Date of deposit | 30 Mar. 2007 (30.03.2007) |
| 4-3-4 | Accession Number | DSMZ 18144 |
| 4-5 | Designated States for Which Indications are Made | all designations |
| 5 | The indications made below relate to the deposited microorganism(s) or other biological material referred to in the description on: | |
| 5-1 | paragraph number | page 13, line 9 |
| 5-3 | Identification of deposit | |
| 5-3-1 | Name of depositary institution | DSMZ DSMZ-Deutsche Sammlung von Mikroorganismen und Zellkulturen GmbH |
| 5-3-2 | Address of depositary institution | Mascheroder Weg 1b, D-38124 Braunschweig, Germany |
| 5-3-3 | Date of deposit | 03 Apr. 2007 (03.04.2007) |
| 5-3-4 | Accession Number | DSMZ 19252 |
| 5-5 | Designated States for Which Indications are Made | all designations |

-continued

| | | |
|---|---|---|
| 6 | The indications made below relate to the deposited microorganism(s) or other biological material referred to in the description on: | |
| 6-1 | paragraph number | page 13, line 10 |
| 6-3 | Identification of deposit | |
| 6-3-1 | Name of depositary institution | DSMZ DSMZ-Deutsche Sammlung von Mikroorganismen und Zellkulturen GmbH |
| 6-3-2 | Address of depositary institution | Mascheroder Weg 1b, D-38124 Braunschweig, Germany |
| 6-3-3 | Date of deposit | 03 Apr. 2007 (03.04.2007) |
| 6-3-4 | Accession Number | DSMZ 19251 |
| 6-5 | Designated States for Which Indications are Made | all designations |
| | FOR RECEIVING OFFICE USE ONLY | |
| 0-4 | This form was received with the international application: (yes or no) | |
| 0-4-1 | Authorized officer | |
| | FOR INTERNATIONAL BUREAU USE ONLY | |
| 0-5 | This form was received by the international Bureau on: | |
| 0-5-1 | Authorized officer | |

The invention claimed is:

1. A method for producing from a mother strain a mutant *Lactobacillus delbrueckii* subsp. *bulgaricus* strain that produces less acid compared to the mother strain when present in a fermented dairy product, comprising:
    (a) treating a culture comprising the mother strain with a mutagen, wherein the mother strain is selected from the group consisting of CHCC3984, CHCC3606, CHCC5713, and mutants thereof that (i) produce a dairy product that has a viscosity of at least 25 Pa in 9.5% milk without the addition of a thickening agent and (ii) decrease the pH of a dairy product more than 0.20 pH units after 7 days of storage at 8° C.; and then
    (b) screening the treated culture for a mutant strain that (i) produces a dairy product that has a viscosity of at least 25 Pa in 9.5% milk without the addition of a thickening agent and (ii) decreases the pH of a dairy product less than 0.20 pH units after 7 days of storage at 8° C.

2. The method of claim 1, wherein the mutagen is ethyl methane sulfonate, nitrous acid, methyl methane sulfonate, nitrosoguanidine, ICR-70 acridine mustard, or radiation.

3. The method of claim 2, wherein the radiation is X-radiation or UV radiation.

4. A mutant strain of *Lactobacillus delbrueckii* subsp. *bulgaricus* produced by the method of claim 1.

5. The strain of claim 4, wherein the strain decreases the pH of a dairy product less than 0.30 pH units after 14 days of storage at 8° C.

6. The strain of claim 4, wherein the strain produces a dairy product that has a pH in the range of 4.25 to 4.55 after 14 days of storage at 8° C.

* * * * *